(12) United States Patent
Joshi et al.

(10) Patent No.: US 7,271,497 B2
(45) Date of Patent: Sep. 18, 2007

(54) DUAL METAL STUD BUMPING FOR FLIP CHIP APPLICATIONS

(75) Inventors: Rajeev Joshi, Cupertino, CA (US); Consuelo Tangpuz, Lapu-Lapu (PH); Margie T. Rios, Mandaue (PH); Erwin Victor R. Cruz, Koronadal (PH)

(73) Assignee: Fairchild Semiconductor Corporation, South Portland, ME (US)

( * ) Notice: Subject to any disclaimer, the term of this patent is extended or adjusted under 35 U.S.C. 154(b) by 0 days.

(21) Appl. No.: 10/386,211

(22) Filed: Mar. 10, 2003

(65) Prior Publication Data

US 2004/0178481 A1 Sep. 16, 2004

(51) Int. Cl.
*H01L 23/52* (2006.01)
*H01L 23/48* (2006.01)
*H01L 29/40* (2006.01)

(52) U.S. Cl. ............... 257/780; 257/779; 257/781; 257/E23.021; 257/678; 228/180.21; 228/180.22; 228/246

(58) Field of Classification Search ........... 257/678, 257/779–781, 784–786, E23.021, E21.508, 257/612; 438/108, 613, 612; 228/180.21, 228/180.22, 246, 254, 208
See application file for complete search history.

(56) References Cited

U.S. PATENT DOCUMENTS

| | | | |
|---|---|---|---|
| 3,650,026 A | | 3/1972 | Freeman |
| 4,005,472 A | * | 1/1977 | Harris et al. ............. 257/737 |
| 4,188,438 A | * | 2/1980 | Burns ..................... 428/209 |
| 4,814,288 A | * | 3/1989 | Kimura et al. ............ 438/206 |
| 4,976,393 A | | 12/1990 | Nakajima et al. |
| 5,169,680 A | * | 12/1992 | Ting et al. ............... 438/629 |
| 5,485,949 A | | 1/1996 | Tomura et al. |
| 5,633,204 A | * | 5/1997 | Tago et al. .............. 438/614 |
| 5,637,916 A | | 6/1997 | Joshi |
| 5,665,996 A | * | 9/1997 | Williams et al. .......... 257/401 |
| 5,740,956 A | * | 4/1998 | Seo et al. ............ 228/180.22 |
| 5,765,280 A | | 6/1998 | Joshi |
| 5,773,889 A | * | 6/1998 | Love et al. .............. 257/737 |

(Continued)

FOREIGN PATENT DOCUMENTS

| | | |
|---|---|---|
| JP | 07-066209 A | 3/1995 |
| JP | 07-312400 A | 11/1995 |
| JP | 07312400 A * | 11/1995 |
| WO | WO 04/081990 A3 | 9/2004 |

OTHER PUBLICATIONS

Zama, Satoru, et al., "Flip Chip Interconnect Systems Using Copper Wire Stud Bump and Lead Free Solder," IEEE Transactions on Electronics Packaging Manufacturing, (Oct. 2001), vol. 24, No. 4, pp: 261-268.

*Primary Examiner*—Kenneth Parker
*Assistant Examiner*—Chris C. Chu
(74) *Attorney, Agent, or Firm*—Townsend and Townsend and Crew LLP

(57) ABSTRACT

A method for forming a stud bumped semiconductor die is disclosed. The method includes forming a ball at the tip of a coated wire passing through a hole in a capillary, where the coated wire has a core and an oxidation-resistant coating. The formed ball is pressed to the conductive region on the semiconductor die. The coated wire is cut, thereby leaving a conductive stud bump on the conductive region, where the conductive stud bump includes an inner conductive portion and an outer oxidation-resistant layer.

13 Claims, 6 Drawing Sheets

U.S. PATENT DOCUMENTS

| | | | |
|---|---|---|---|
| 5,789,809 A | 8/1998 | Joshi | |
| 5,813,115 A * | 9/1998 | Misawa et al. | 29/832 |
| 5,829,128 A * | 11/1998 | Eldridge et al. | 29/855 |
| 5,844,320 A * | 12/1998 | Ono et al. | 257/778 |
| 5,906,312 A * | 5/1999 | Zakel et al. | 228/246 |
| 5,908,317 A * | 6/1999 | Heo | 438/617 |
| 5,933,711 A * | 8/1999 | Cho | 438/123 |
| 5,969,418 A * | 10/1999 | Belanger, Jr. | 257/737 |
| 6,023,094 A | 2/2000 | Kao et al. | |
| 6,084,308 A | 7/2000 | Kelkar et al. | |
| 6,103,551 A * | 8/2000 | Ono et al. | 438/108 |
| 6,104,201 A * | 8/2000 | Beaman et al. | 324/755 |
| 6,133,634 A | 10/2000 | Joshi | |
| 6,175,162 B1 | 1/2001 | Kao et al. | |
| 6,246,011 B1 * | 6/2001 | Abraham et al. | 174/260 |
| 6,294,403 B1 | 9/2001 | Joshi | |
| 6,469,384 B2 | 10/2002 | Joshi | |
| 6,482,676 B2 * | 11/2002 | Tsunoi et al. | 438/108 |
| 6,489,678 B1 | 12/2002 | Joshi | |
| 6,492,593 B2 | 12/2002 | Murai et al. | |
| 6,495,397 B2 * | 12/2002 | Kubota et al. | 438/108 |
| 6,500,760 B1 * | 12/2002 | Peterson et al. | 438/684 |
| 6,566,749 B1 | 5/2003 | Joshi et al. | |
| 6,646,357 B2 * | 11/2003 | Takaike | 257/784 |
| 6,653,170 B1 * | 11/2003 | Lin | 438/117 |
| 6,784,543 B2 * | 8/2004 | Matsuki et al. | 257/746 |
| 2003/0173659 A1 | 9/2003 | Lee et al. | |

* cited by examiner

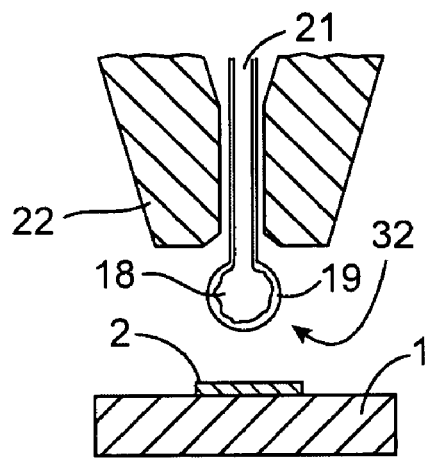
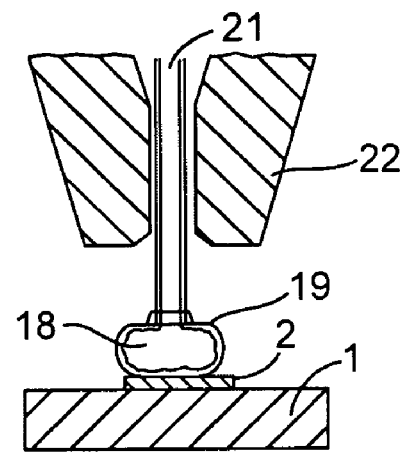
FIG. 4     FIG. 5
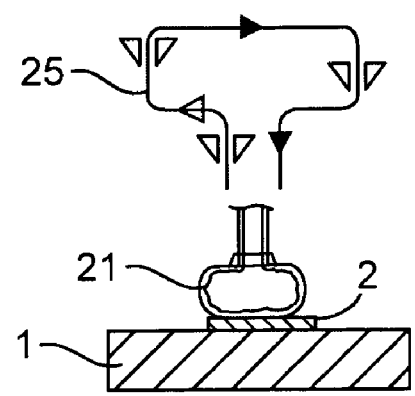
FIG. 6

DUAL METAL STUD BUMPING FOR FLIP CHIP APPLICATIONS

BACKGROUND OF THE INVENTION

There are many different levels of packages and interconnections in electronic packages. In a typical first level packaging process, a silicon die is joined to a ceramic substrate carrier. In a typical second level packaging process, the ceramic substrate carrier with the die is mounted on an organic board.

In one conventional method for forming a first level package, a passivation layer is formed on a semiconductor die (which may be in a semiconductor wafer). The passivation layer includes apertures that expose conductive regions on the semiconductor die. Titanium and copper layers are sputtered on the upper surface of the conductive regions and the passivation layer. A layer of photoresist is then patterned on the semiconductor die so that the apertures in the patterned photoresist layer are over the conductive regions. Solder is electroplated in the apertures in the photoresist layer until the apertures are filled with solder. The photoresist is stripped and the portions of the titanium and copper layers around the solder deposits are removed. Then, the solder deposits are subjected to a full reflow process. The full reflow process causes the solder deposits to form solder balls. After forming the solder balls, the semiconductor die is bonded face-down to a carrier. The solder balls on the semiconductor die contact conductive regions on the chip carrier. Non-soluble barriers are disposed around the conductive regions and constrain the solder balls. The solder balls between the conductive regions on the carrier and the semiconductor die melt and wet the conductive regions on the carrier. Surface tension prevents the melting solder from completely collapsing and holds the semiconductor die suspended above the carrier.

During the reflow step, the deposited solder substantially deforms into solder balls. Because of the deformation, the heights of the resulting solder balls on the semiconductor die can be uneven. If the heights of the solder balls are uneven, the solder balls may not all contact the conductive regions of the carrier simultaneously when the semiconductor die is mounted to the chip carrier. If this happens, the strength of the formed solder joints may be weak thus potentially decreasing the reliability of the formed package. Moreover, during the reflow process, the deposited solder is exposed to high temperatures for extended periods of time. Excessively heating the deposited solder can promote excessive intermetallic growth in the solder deposits. Intermetallics in the solder joints make the solder joints brittle and reduce the fatigue resistance of the solder joints. Lastly, performing a full reflow process takes time and energy and thus adds to the cost of the die package that is finally produced. If possible, it would be desirable to reduce the time and energy associated with the full reflow process.

One approach to solving the above problems is to use a "stud bumping" technique to form a copper stud on the conductive regions, instead of solder. The copper stud is formed using a wire bonding technique where an end of a wire forms a ball, which is compressed to a conductive region of a semiconductor die. The wire is then cut leaving the compressed ball, which is in the form of a copper stud. The semiconductor die is then flipped over and is then mounted to a carrier of a circuit board having conductive lands with Pb—Sb—Sn solder.

While the described stud bumping approach is feasible, there are some problems to be addressed. First, in the above-described approach, a thick intermetallic compound layer can form between the copper stud and the Pb—Sb—Sn solder. The thick intermetallic compound layer can increase the "on resistance" of the die package. Second, voids can form between the copper in the copper stud and the thick intermetallic compound layer. As shown in FIG. 1, for example, after testing for 1000 hours at 150° C., a gap (or void) is shown between a formed intermetallic compound layer and the copper stud. The gap results in a poor electrical and mechanical connection between the semiconductor die and the carrier to which it is attached. Without being bound by theory, the inventors believe that the void formation at the copper/intermetallic compound interface is caused by either copper oxidation and/or the differences in diffusion rates of Cu, Sn, and Sb.

Embodiments of the invention address these and other problems.

SUMMARY OF THE INVENTION

Embodiments of the invention are directed to stud bumped semiconductor dies, semiconductor die packages formed using the bumped semiconductor dies, and methods for making the same.

One embodiment of the invention is directed to a method comprising: (a) forming a ball at the tip of a coated wire passing through a hole in a capillary, wherein the coated wire comprises a core and an outer oxidation-resistant coating; (b) pressing the ball to a conductive region on a semiconductor die; and (c) cutting the coated wire, thereby leaving a conductive stud bump on the conductive region, wherein the conductive stud bump includes an inner conductive portion and an outer oxidation-resistant layer.

Another embodiment of the invention is directed to a bumped semiconductor die comprising: (a) a semiconductor die including a conductive region; and (b) a conductive stud bump on the conductive region, wherein the conductive stud bump includes an inner conductive portion and an outer oxidation-resistant layer.

Another embodiment of the invention is directed to a semiconductor die package comprising: (a) a bumped semiconductor die comprising (i) a semiconductor die including a first conductive region, and (ii) a conductive stud bump on the conductive region, wherein the conductive stud bump includes an inner conductive portion and an outer oxidation-resistant layer; and (b) a circuit substrate including a second conductive region, and solder on the second conductive region, wherein the bumped semiconductor die is mounted on the circuit substrate and the conductive stud bump contacts the solder on the second conductive region.

These and other embodiments of the invention are described in further detail below.

BRIEF DESCRIPTION OF THE DRAWINGS

FIGS. 4-7 show cross-sections of a coated wire, capillary, and semiconductor die during a process of forming a conductive stud bump.

The sizes of the various elements in the Figures may not be to scale for ease of illustration. Also, in the Figures, like numerals designate like elements.

DETAILED DESCRIPTION

Figure 1A:
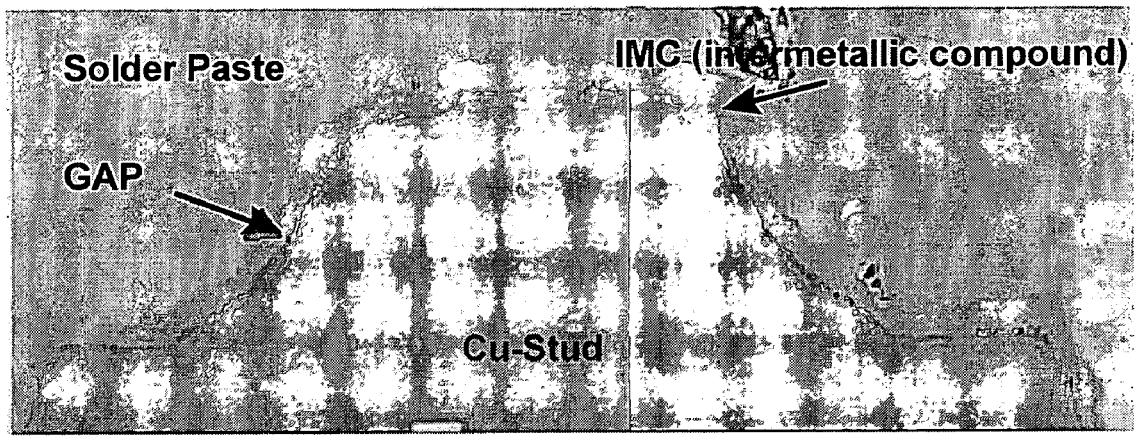
FIG. 1(a) shows a cross-sectional photograph of a copper stud, solder paste, and, an intermetallic compound layer between the copper stud and solder paste.
Figure 1B:
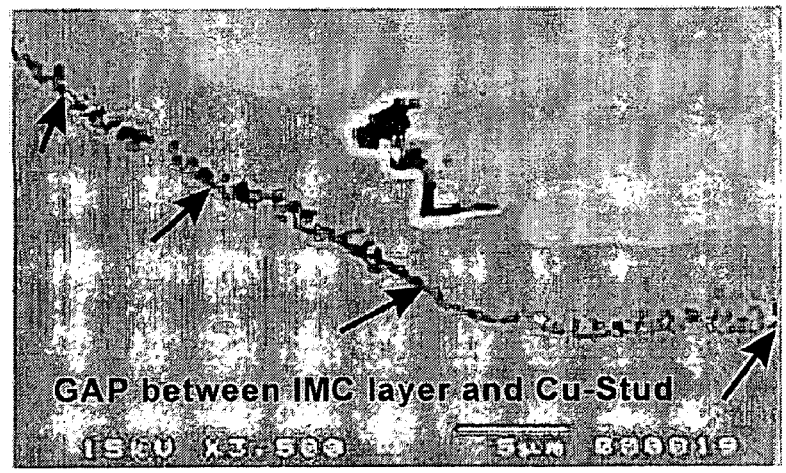
FIG. 1(b) shows a gap that forms between the intermetallic layer and the copper stud.
Figure 2:
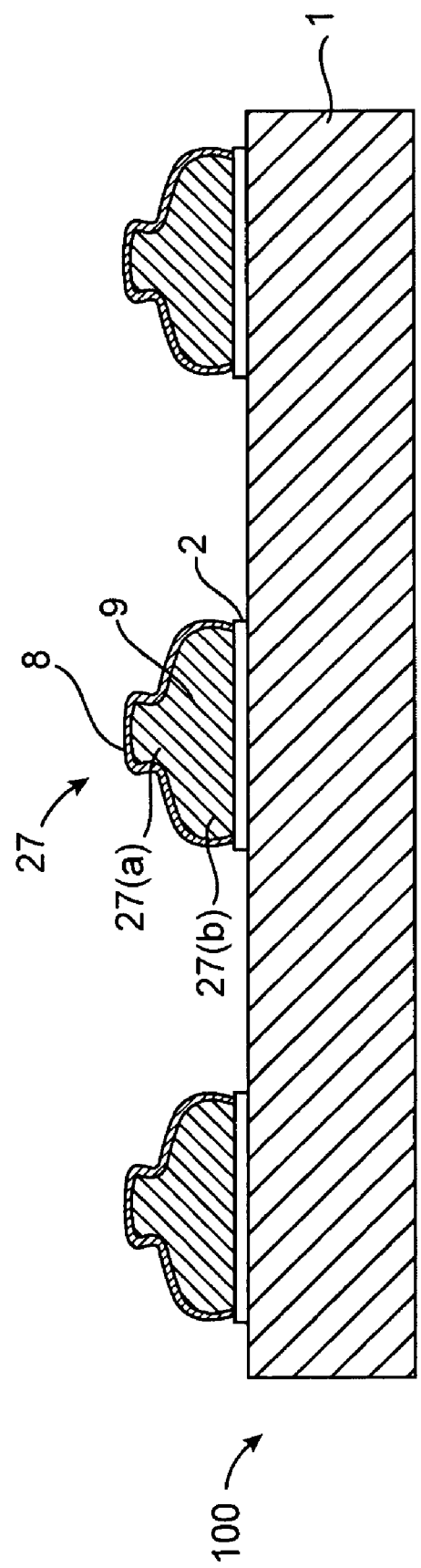
FIG. 2 shows a cross-section of a semiconductor die with conductive stud bumps on it.

FIG. 2 shows a stud bumped semiconductor die 100 according to an embodiment of the invention. The stud bumped semiconductor die 100 has a semiconductor die 1 including first conductive regions 2, and conductive stud bumps 27 on the first conductive regions 2.

The semiconductor die 100 may comprise any suitable material (e.g., silicon, gallium arsenide) and may include any suitable active or passive semiconductor device. For example, the semiconductor die may comprise a metal oxide field effect transistor (MOSFET) such as a power MOSFET. The MOSFET may have a planar or trenched gate. Trenched gates are preferred. Transistor cells containing trenched gates are narrower than planar gates. In addition, the MOSFET may be a vertical MOSFET. In a vertical MOSFET, the source region and the drain region are at opposite sides of the semiconductor die so that current in the transistor flows vertically through the semiconductor die.

Each conductive region 2 may be, for example, a conductive land. Each conductive region 2 may also comprise one or more layers of material. For example, a conductive region according to an embodiment of the invention may comprise a layer of aluminum with one or more underbump metallurgy layers including Ti, Ni, Cr, etc.

Each conductive stud bump 27 may include an inner conductive portion 9 and an outer oxidation-resistant layer 8. Each conductive stud bump 27 also includes a head 27(*a*) and a base 27(*b*). As shown, the head 27(*a*) is narrower than the base 27(*b*). If the semiconductor die 1 comprises a power MOSFET such as a vertical power MOSFET, the conductive stud bumps 27 can be connected to the source and gate regions of the MOSFET.

The inner conductive portion 9 preferably comprises copper (e.g., pure copper or a copper alloy). The outer oxidation-resistant layer 8 comprises a material that resists oxidation. Suitable materials include noble metals (and alloys thereof) such as Pd, Pt, Au, Ag, etc. Although the illustrated embodiment shows a conductive stud bump 27 with two distinct regions (i.e., the inner conductive portion 9 and the oxidation-resistant layer 8), it is understood that the conductive stud bumps according to embodiments of the invention may have any suitable number of distinct regions.

The oxidation-resistant layer 8 can have any suitable thickness. For example, it may have a thickness of about 0.01 to about 0.5 microns in some embodiments. The oxidation-resistant layer 8 can coat at least one of the sides, top, and bottom of the inner conductive portion 9, and may be the outermost layer in the conductive stud bump 27.

Figure 3:
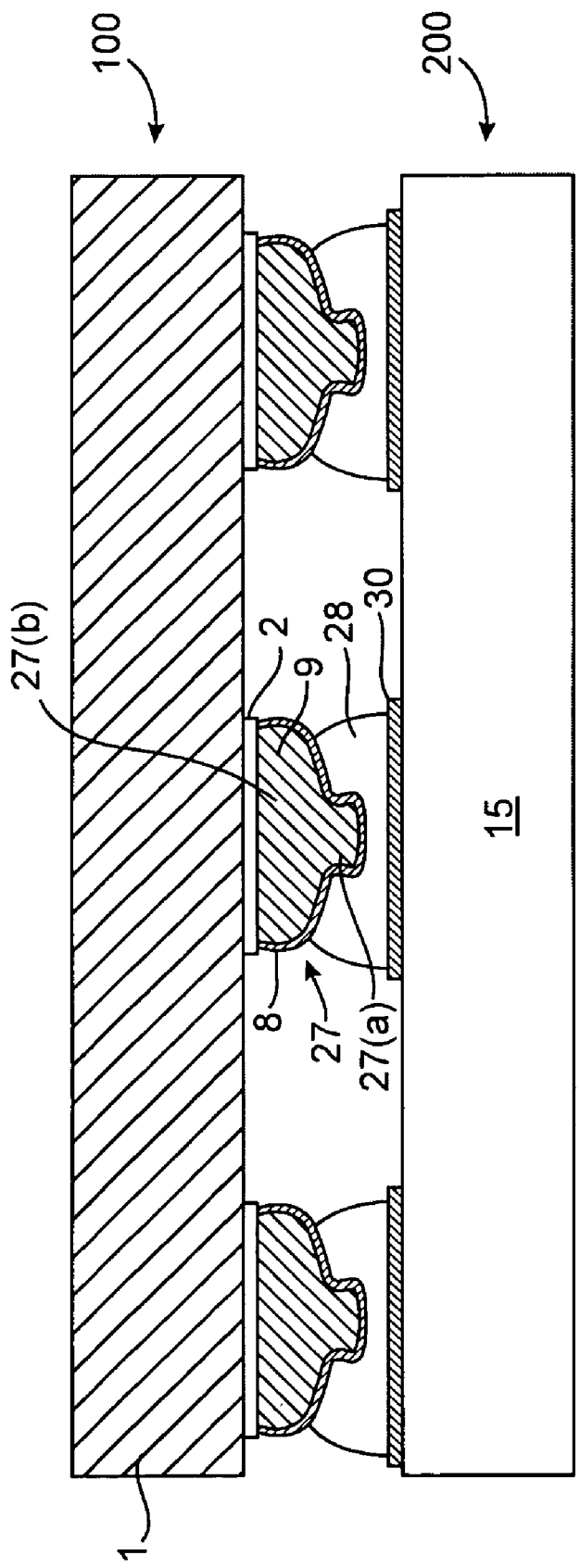
FIG. 3 shows a cross-section of a semiconductor die with conductive stud bumps mounted on a circuit substrate.

FIG. 3 shows how the stud bumped semiconductor die 100 can be mounted to a circuit substrate 200. The circuit substrate 200 may include a number of second conductive regions 30 on a base substrate 15. The base substrate 15 may include one or more dielectric layers (e.g., ceramic or polymeric dielectric layers), and could also include conductive layers between adjacent dielectric layers. The circuit substrate 200 could be a carrier for a semiconductor die, a circuit board, or any other electrical device for supporting a semiconductor die. For example, the circuit substrate 200 could alternatively be a leadframe with leads. After mounting the bumped semiconductor die 100 to the leadframe, an inner portion of the leadframe and the bumped semiconductor die 100 can be encapsulated in a molding compound.

As shown, the second conductive regions 30 may have solder deposits 28 on them. Each solder deposit 28 may comprise, for example, solder including a material such Pb, Sn, and optionally, Sb. In other embodiments, the solder could be a lead-free solder such as a solder comprising Sn, Ag, and Sb. The solder deposits 28 may be on the second conductive regions 30 before the stud bumped semiconductor die 100 is flipped over and is mounted on the circuit substrate 200. The solder deposits 28 can be deposited using any suitable process including a screening process, a pick and place process, or electroplating process or solder dispensing process.

As shown in FIG. 3, the stud bumped semiconductor die 100 may be flipped over and then the heads 27(*a*) of the conductive stud bumps 27 can penetrate the solder deposits 28 and may thereafter electrically connect the first conductive regions 2 and the second conductive regions 30. A solder reflow process may be performed after mounting. Reflow processes are well known in the art and need not be described in further detail here. This provides electrical connections between the semiconductor die 1 and the circuit substrate 200.

The oxidation-resistant layer 8 of the conductive stud bump 27 protects the inner conductive portion 9 from oxidizing. This reduces the likelihood of forming voids between the inner conductive portions 9 of the conductive stud bumps 27, and the solder deposits 28. As explained above, the formation of voids is believed to be caused by copper oxide and/or differences in the diffusion rates of atoms such as Cu, Sn, and Sb (e.g., for a pure copper stud that contacts a Pb—Sb—Sn solder).

Some embodiments of the invention are directed to methods for forming the above-described stud bumped semiconductor die 100. A suitable method includes forming a ball at the tip of a coated wire passing through a hole in a capillary. The coated wire comprises a core and an outer oxidation-resistant coating. The ball is then pressed to a conductive region on a semiconductor die using ultrasonic energy and/or heat to bond the ball to the conductive region. Then, the coated wire is cut, thereby leaving a conductive stud bump on the conductive region. The conductive stud bump may then be optionally leveled to make its height consistent with other conductive stud bumps.

As described above, the resulting conductive stud bump includes an inner conductive portion and an outer oxidation-resistant layer. Then, as described above, the bumped semiconductor die is mounted on a circuit substrate. The circuit substrate includes a conductive region and solder on the conductive region, wherein the solder on the conductive region contacts the conductive stud bump.

A method for forming a conductive stud bump on a semiconductor die can be described with reference to FIGS. 4-7. FIG. 4 shows a composite ball 32 that forms at the leading end of a coated wire 21. The coated wire 21 is fed through a capillary 22 and the composite ball 32 forms at the end of the capillary 22. Thermal energy and/or sonic energy is applied to the end of the coated wire 21 by using, for example, a gas flame, electric pulses, ultrasonic energy, or the like.

The coated wire 21 and the composite ball 32 each comprise a conductive core 18 and an outer oxidation-resistant coating 19. The coated wire 21 may have a diameter less than about 1 mm. The thickness of the oxidation-resistant coating 19 may be on the order of about 0.01 to about 0.5 microns in some embodiments. The conductive core 18 may comprise copper (or a copper alloy) and the oxidation-resistant coating 19 may comprise a noble metal such as Pd (or alloy thereof).

The capillary 22 (with ultrasonic energy and/or heat) can be used to compress the composite ball 32 to the first conductive region 2 of the semiconductor die 1. By using a thermo-compression bonding process, and/or by using ultrasonic energy, the composite ball 32 is secured to the first conductive region 2. The pressure applied to the composite ball 32 may vary, and could be, for example, about 20 to about 45 grams per composite ball 32. The ultrasonic energy that can be applied may be in the range of 60 kHz.

Figure 7:
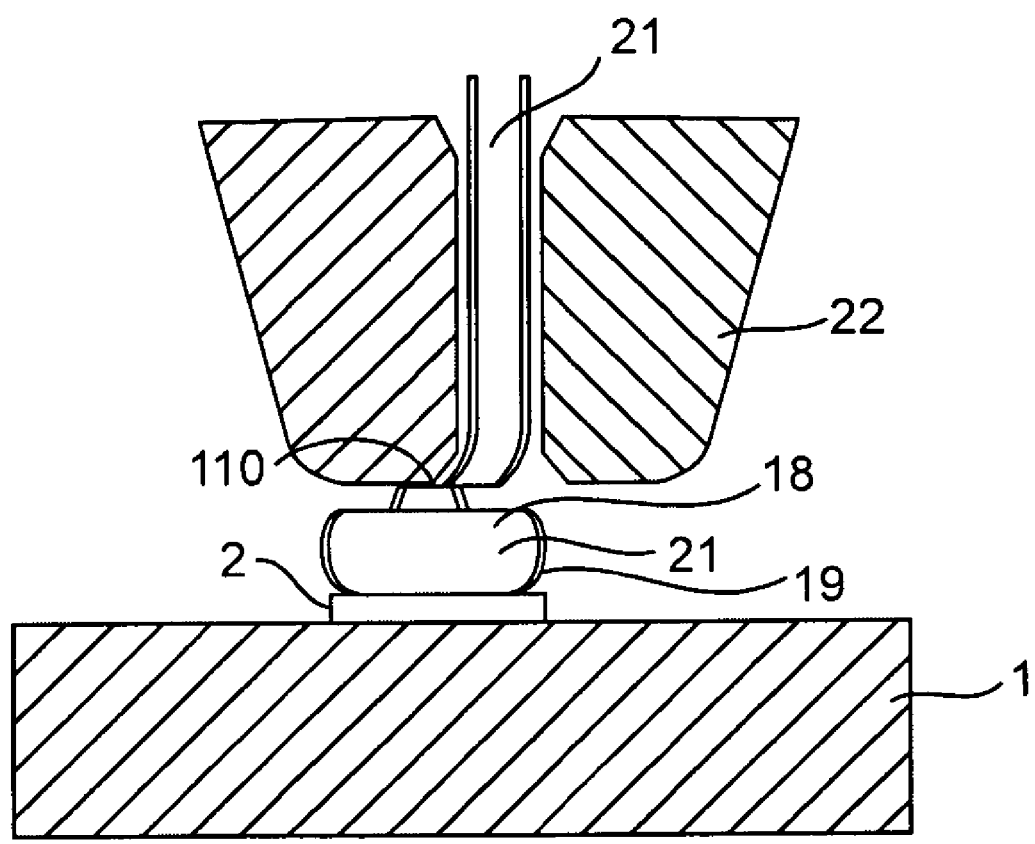

Thereafter, the capillary 22 moves along a path 25 forming a loop shown in FIG. 6 and, as the capillary 22 moves downward as shown in FIG. 7, the coated wire 21 is cut with the edge 110 of the capillary 22. An inert or reducing gas such as nitrogen or $N_2H_2$ can be supplied to the conductive stud bump as it is being formed to reduce the likelihood of forming oxides.

Next, the resulting conductive stud bump can be subjected to leveling by applying pressure (with a flat surface) to the upper surface of the conductive stud bump. By applying pressure (e.g., of about 50 g/bump) to the top of a recently formed conductive stud bump, it is possible to make the height of the bump consistent with other bumps.

An apparatus for performing the above process is commercially available from ASM, Inc. of Singapore (e.g., ASM AB339). A KNS1488L turbo conventional wire bonder, commercially available from Kulicke & Soffa of Willow Grove, Pa., could also be used.

Figure 8:
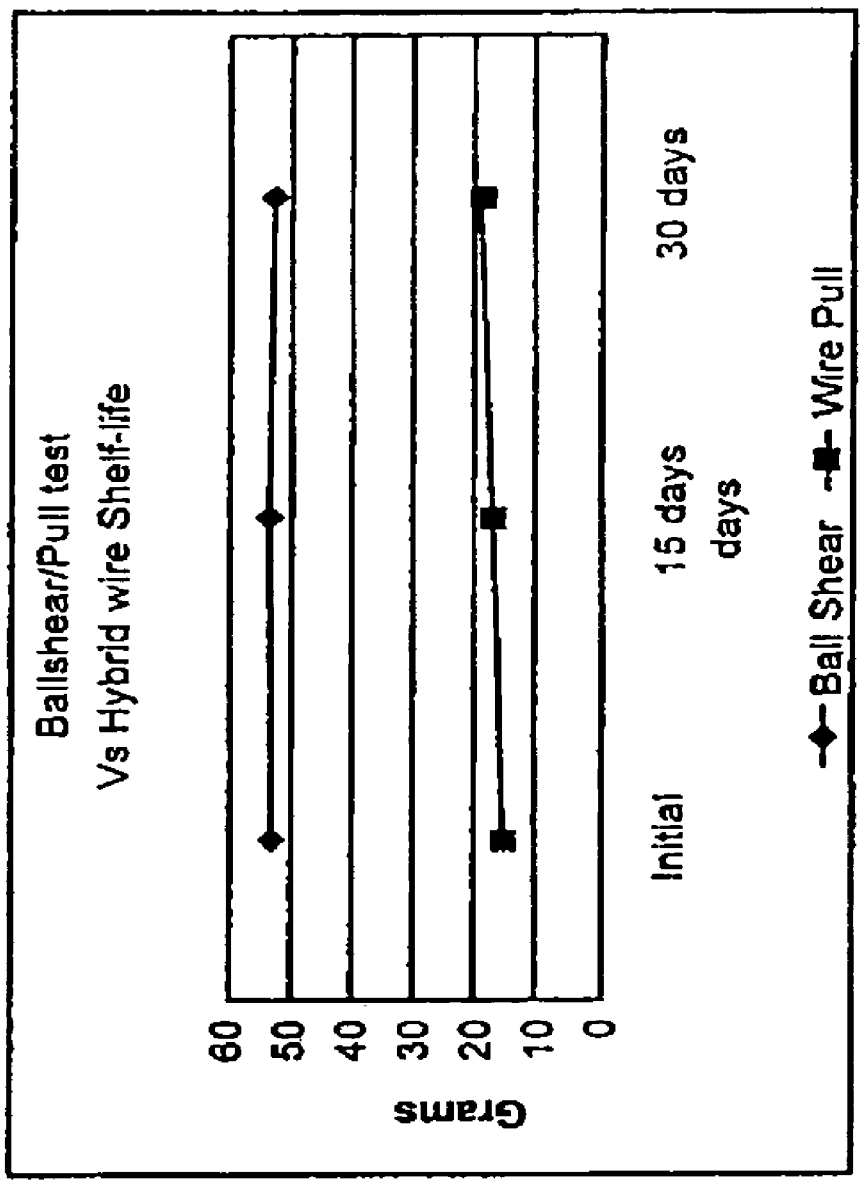
FIG. 8 is a graph showing ball shear/pull test strength over time for a ball that is bonded to a conductive region of a semiconductor die using a coated wire including a copper core and an outer coating including palladium.

Using a coated wire in the stud-bumping process described above has a number of advantages. First, the copper in the formed conductive stud bumps according to embodiments of the invention is protected by the oxidation-resistant layer and the conductive stud bumps have a better pull strength as compared to stud bumps that have only copper in them. FIG. 8, for example, shows a graph showing ball shear/pull test strength over time for a ball that is bonded to a conductive region of a semiconductor die using a coated wire including a copper core and an outer coating including palladium. As shown in the graph, the shear strength and pull strength of a ball that is bonded to a conductive region of a semiconductor die are high. Second, the coated wires that are used in embodiments of the invention have a long shelf-life and a long process life-time. The oxidation-resistant coating in a coated wire protects the core of the wire from becoming oxidized, thereby improving its shelf-life. Third, as compared to a Cu stud bump formed from a copper wire, a Cu/Pd stud bump formed from a Cu/Pd wire reduces the likelihood of forming voids at the Cu/intermetallic compound interface. This improves the overall reliability of a package that is formed using the coated wire. Fourth, the oxidation-resistant layer in the conductive stud bump prevents oxidation of the inner conductive portion, thereby improving the reliability of the conductive stud bump over time. Fifth, the oxidation-resistant layer in the conductive stud bump acts as a barrier metal for the formation of intermetallics that are formed due to the common use of solder materials. Sixth, embodiments of the invention provide a robust, solderable interface between the bump and the circuit substrate. Seventh, since a substantially solid conductive stud bump is used in embodiments of the invention, less solder can be used as compared to a process that uses only solder as an interconnect material. Consequently, a full reflow process (as described above) need not be performed so that the likelihood of forming intermetallic compounds is reduced in embodiments of the invention.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention.

What is claimed is:

1. A semiconductor die package comprising:
   (a) a bumped semiconductor die comprising (i) a semiconductor die including a first planar conductive region, and (ii) a conductive stud bump on the first planar conductive region, wherein the conductive stud bump consists of a distinct inner conductive portion comprising copper and a distinct outer oxidation-resistant layer, wherein the inner conductive portion is in direct contact with the outer oxidation resistant layer; and
   (b) a circuit substrate including a second conductive region, and solder on the second conductive region,
   wherein the bumped semiconductor die is mounted on the circuit substrate and the conductive stud bump contacts the solder on the second conductive region,
   wherein the conductive stud bump comprises a base and a head, wherein the base is wider than the head, and wherein the oxidation-resistant layer comprises a noble metal,
   wherein portions of the oxidation-resistant layer and the inner conductive portion forming the base contact the first planar conductive region.

2. The semiconductor die package of claim 1 wherein the solder comprises Pb and Sn, or a Pb-free solder.

3. The semiconductor die package of claim 2 wherein the oxidation-resistant layer has a thickness between about 0.01 to about 0.5 microns.

4. The semiconductor die package of claim 1 wherein the semiconductor die comprises a vertical power MOSFET.

5. The semiconductor die package of claim 1 wherein the oxidation-resistant layer has a thickness between about 0.01 to about 0.5 microns.

6. The semiconductor die package of claim 1 wherein the solder is between the semiconductor die and the circuit substrate.

7. A bumped semiconductor die comprising:
   (a) a semiconductor die including a planar conductive region; and
   (b) a conductive stud bump on the planar conductive region, wherein the conductive stud bump includes an inner conductive portion comprising copper and an outer oxidation-resistant layer, wherein the conductive stud bump comprises a base and a head, wherein the base is wider than the head, and wherein the oxidation-resistant layer comprises a noble metal,
   wherein portions of the oxidation-resistant layer and the inner conductive portion forming the base contact the planar conductive region, and wherein the conductive stud bump exhibits a ball shear pull strength of at least 50 grams for over 30 days and a wire pull strength of at least 10 grams for over 30 days.

8. The bumped semiconductor die of claim 7 wherein the semiconductor die comprises a vertical power MOSFET including a trenched gate region at one side of the die and a drain region at the other side of the die.

9. The bumped semiconductor die of claim 7 wherein the oxidation-resistant layer has a thickness between about 0.01 to about 0.5 microns.

10. A semiconductor die package comprising:
(a) a bumped semiconductor die comprising (i) a semiconductor die including a first planar conductive region, and (ii) a conductive stud bump on the first planar conductive region, wherein the conductive stud bump includes an inner conductive portion comprising copper and an outer oxidation-resistant layer; and
(b) a circuit substrate including a second conductive region, and solder on the second conductive region,
wherein the bumped semiconductor die is mounted on the circuit substrate and the conductive stud bump contacts the solder on the second conductive region,
wherein the conductive stud bump comprises a base and a head, wherein the base is wider than the head, and
wherein the oxidation-resistant layer comprises a noble metal, and
wherein the conductive stud bump exhibits a ball shear pull strength of at least 50 grams at 30 days and a wire pull strength of at least 10 grams at 30 days.

11. The semiconductor die package of claim 10 wherein the semiconductor die comprises a vertical power MOSFET including a trenched gate region at one side of the die and a drain region at the other side of the die.

12. The semiconductor die package of claim 10 wherein the oxidation-resistant layer has a thickness between about 0.01 to about 0.5 microns.

13. The semiconductor die package of claim 10 wherein the solder is between the semiconductor die and the circuit substrate.

* * * * *